United States Patent [19]

Rentzea et al.

[11] Patent Number: 4,967,003
[45] Date of Patent: Oct. 30, 1990

[54] PROPYLAMINES, AND THEIR USE AS FUNGICIDES

[75] Inventors: Costin Rentzea, Heidelberg; Walter Himmele, Walldorf; Ernst Buschmann; Eberhard Ammermann, both of Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 928,006

[22] Filed: Nov. 7, 1986

[30] Foreign Application Priority Data

Nov. 21, 1985 [DE] Fed. Rep. of Germany ....... 3541181

[51] Int. Cl.$^5$ ............................................. C07C 87/28
[52] U.S. Cl. ..................................... 564/381; 514/520; 514/654; 514/659; 558/411; 564/462
[58] Field of Search ............... 564/374, 375, 381, 462, 564/454

[56] References Cited

U.S. PATENT DOCUMENTS

| | | | |
|---|---|---|---|
| 3,079,403 | 2/1963 | Weinstock | 564/462 X |
| 3,254,124 | 5/1966 | Stevero | 564/462 X |
| 3,994,914 | 11/1976 | Easton et al. | 564/462 X |
| 4,139,560 | 2/1979 | Reinehr et al. | 564/462 X |
| 4,487,965 | 12/1984 | Himmele et al. | 564/454 |

FOREIGN PATENT DOCUMENTS

| | | | |
|---|---|---|---|
| 0058326 | 8/1982 | European Pat. Off. | 564/370 |
| 2825961 | 1/1980 | Fed. Rep. of Germany | 564/374 |
| 988630 | 4/1965 | United Kingdom . | |

*Primary Examiner*—Robert V. Hines
*Attorney, Agent, or Firm*—Oblon, Spivak, McClelland, Maier & Neustadt

[57] ABSTRACT

N-Arylpropyl-substituted secondary amines of the formula

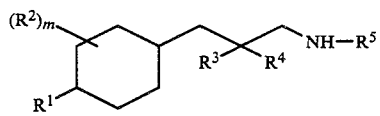

where $R^1$ and $R^2$ are each hydrogen, alkyl, cycloalkyl, haloalkyl, alkoxy, chlorine, bromine or fluorine, m is 0, 1 or 2, $R^3$ and $R^4$ are each hydrogen or alkyl, and $R^5$ is alkyl, cycloalkyl, cycloalkenyl, cycloalkylalkyl, alkenyl or an unsubstituted or substituted phenyl or phenylalkyl radical or methylfuran and the dashed bonds may be hydrogenated, and their salts, and fungicides containing these compounds.

2 Claims, No Drawings

PROPYLAMINES, AND THEIR USE AS FUNGICIDES

The present invention relates to novel propylamines, processes for their preparation, their use as fungicides, fungicides which contain the novel active ingredients, processes for the preparation of such fungicides and methods for controlling harmful fungi with these fungicides.

It has been disclosed that N-tridecyl-2,6-dimethylmorpholine can be used as a fungicide (DE 1 164 152).

We have found that compounds of the formula I

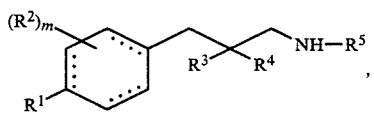

where $R^1$ and $R^2$ are identical or different and are each hydrogen, alkyl of 1 to 8 carbon atoms, cycloalkyl of 3 to 9 carbon atoms, haloalkyl of 1 to 3 halogen atoms and 1 to 4 carbon atoms, alkoxy of 1 to 3 carbon atoms, chlorine, bromine or fluorine, m is the integer 0, 1 or 2, $R^1$ being $C_1-C_8$-alkyl or $C_3-C_9$-cycloalkyl and $R^2$ being hydrogen where the dashed bonds are hydrogenated, and $R^3$ and $R^4$ independently of one another are each hydrogen or $C_1-C_5$-alkyl and $R^5$ is alkyl of 1 to 10 carbon atoms, cycloalkyl of 3 to 12 carbon atoms, cycloalkenyl of 5 to 12 carbon atoms, cycloalkylalkyl of 4 to 13 carbon atoms, alkenyl of 3 to 6 carbon atoms or a phenyl or phenyl-$C_1-C_6$-alkyl radical which is unsubstituted or substituted by halogen, $C_1-C_4$-alkyl, halo-$C_1-C_4$-alkyl, $C_1-C_4$-alkoxy or cyano, and the dashed bonds may be hydrogenated, and their salts possess excellent activity against harmful fungi and are well tolerated by plants.

The novel amines of the formula I may contain chiral centers. They are generally obtained in the form of racemates and may be obtained as diastereomer mixtures. In the case of some of the novel compounds, single diasteroemers can be isolated in pure form, for example by column chromatography or on the basis of solubility differences. Pure racemates and enantiomers can be obtained from such purified diastereomers by a conventional method. All these compounds and mixtures are embraced by the present invention. Regarding the use of the novel amines, both the pure diastereomers of enantiomers and the mixtures of these obtained in the synthesis are suitable as fungicides. The said mixtures are preferably used.

$R^1$ and $R^2$ are each, for example, hydrogen, fluorine, chlorine, bromine, trifluoromethyl, methoxy, ethoxy, propoxy, methyl, ethyl, straight-chain or branched propyl, butyl, pentyl, hexyl, heptyl, octyl, cyclopentyl, cyclohexyl, methyl-, dimethyl- or trimethylcyclohexyl or norbornyl.

$R^3$ and $R^4$ are each, for example, hydrogen, methyl, ethyl, straight-chain or branched propyl, butyl or pentyl.

$R^5$ is, for example, $C_1-C_{10}$-alkyl, methyl, ethyl, straight-chain or branched propyl, butyl, pentyl, hexyl, heptyl, octyl, nonyl, decyl, $C_2-C_6$-alkenyl, allyl, methallyl, pentenyl, hexenyl, $C_3-C_{12}$-cycloalkyl, cyclopropyl, cyclopropylmethyl, cyclopentyl, methylcyclopentyl, cyclopentylmethyl, cyclohexyl, cyclohexylmethyl, cyclohexylethyl, cyclohexylpropyl, di-, tri- or tetramethylcyclohexyl, ethylcyclohexyl, propyl- or isopropylcyclohexyl, butyl, isobutyl, sec-butyl- or tert-butylcyclohexyl, tert-amylcyclohexyl, cyclohexylcyclohexyl, methyl, phenylcyclohexyl, cycloheptyl, cycloheptylmethyl, methylcycloheptyl, propylcycloheptyl, cyclooctyl, cyclododecyl, cyclododecylmethyl, $C_5-C_{12}$-cycloalkenyl, cyclopentenyl, α-campholenyl, cyclohexenylmethyl, tert-butylcyclohexenyl, tert-butylcyclohexylpropyl-, tert-butylcyclohexenyl-, tert-butylcyclohexenylpropyl, cycloheptenyl, cyclooctenyl, cyclododecadienyl, cyclododecadienylmethyl, decalyl, norbornyl, tricyclodecyl, 1,5-dimethylbicyclo[2.3.1]oct-8-yl, isobornyl, adamantyl, norbornylmethyl, camphenyl, homocamphenyl, pinanyl, norborneyl, nopolyl, phenyl, chlorophenyl, dichlorophenyl, alkoxyphenyl, alkylphenyl, phenyl-$C_1-C_6$-alkyl, benzyl, halophenyl-$C_1-C_4$-alkyl, chlorobenzyl, fluorobenzyl, methylbenzyl, ethylbenzyl, propylbenzyl, butylbenzyl, methoxybenzyl, trifluoromethylbenzyl, phenylethyl, 1-phenyl-2-$C_1-C_2$-alkylprop-3-yl, 1-(4-tert-butylphenyl)-2-methylprop-3-yl, chlorophenylpropyl, dichlorophenylpropyl, fluorophenylpropyl, phenylpropyl, phenylbutyl, phenylpentyl, phenylhexyl or 2-methylfuran.

O=C [R'5] is, for example, formaldehyde, acetaldehyde, acetone, butanone or benzaldehyde.

The amines of the formula I can be prepared if
(a) an aldehyde of the formula II is reacted with an amine of the formula III

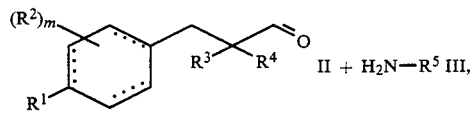

where $R^1$, $R^2$, $R^3$, $R^4$, $R^5$, m and the dashed bonds have the above meanings, or (b) an amine of the formula IV is reacted with an aldehyde or ketone of the formula V

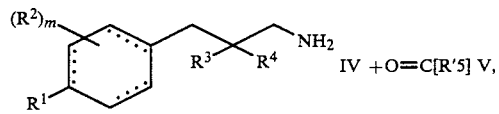

where $R^1$, $R^2$, $R^3$, $R^4$, m and the dashed bonds have the above meanings, O=C[R'5] is the aldehyde or ketone of the radical $R^5$ and $R^5$ may furthermore be $C_3-C_6$-alkenyl or $C_5-C_{12}$-cycloalkenyl, in the presence of formic acid or sodium borohydride or sodium cyanoborohydride or in the presence of hydrogen and a catalyst, such as Ni, Pd or Pt, or (c) a compound of the formula VI is reacted with an amine of the formula III

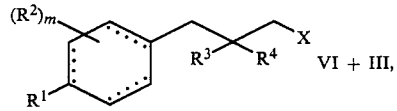

where $R^1$, $R^2$, $R^3$, $R^4$, m, III and the dashed bonds have the above meanings and X is a leaving group which can be displaced by a nucleophilic substitution, or (d) an alkylating agent of the formula VII is reacted with an amine of the formula IV $$IV + X-R^5 \qquad VII,$$

where IV, X and $R^5$ have the above meanings, and the resulting compound is, if required, converted to its salts.

In versions (a) and (b) of the process, amines of the formula III or IV are reacted with aldehydes of the formula II or V in the presence of formic acid. This reductive alkylation is preferably carried out in the absence of solution. To dissolve the amine in formic acid, the aldehyde is added dropwise at from 0° to 110° C., preferably from 50° to 100° C.

In contrast, the reactions of the aldehydes II or V with amines of the formula III or IV are carried out in the presence of sodium borohydride or sodium cyanoborohydride in a solvent or diluent. Alcohols, such as methanol, ethanol, propanol or isopropanol, which may contain up to 25% by volume of water, are preferably used for this purpose.

In versions (a) and (b) of the process, amines of the formula III or IV may furthermore by alkylated with aldehydes of the formula II or V in the presence of hydrogen and a catalyst.

Suitable catalysts are noble metals, for example palladium, platinum (if necessary deposited on a carrier), rhodium and Raney nickel. Palladium on carbon is preferred. Suitable solvents are alcohols, such as methanol or ethanol, hydrocarbons, such as hexane, heptane, octane, cyclohexane, toluene or xylene. If perhydrogenation is desired, platinum in glacial acetic acid is used as the catalyst, with the addition of perchloric acid. Under these conditions, the aromatic radical is completely hydrogenated.

Examples of suitable solvents or diluents for all three versions (a), (b) and (c) of the process are halohydrocarbons, in particular chlorohydrocarbons, e.g. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1-or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m- or p-chlorotoluene or 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, ethylene glycol dimethyl ether, tetrahydrofuran, dioxane, thioanisole or $\beta,\beta,\beta'$-dichlorodiethyl ether; nitrohydrocarbons, such as nitromethane, nitroethane, nitrobenzene, o-, m- or p-chloronitrobenzene or o-nitrotoluene; nitriles, such as acetonitrile, butyronitrile, isobutyronitrile, benzonitrile or m-chlorobenzonitrile; aliphatic or cycloaliphatic hydrocarbons, e.g. heptane, pinane, nonane, o-, m- or p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane of octane; esters, e.g. ethyl acetate, ethyl acetoacetate or isobutyl acetate; amides, e.g. formamide, methylformamide or dimethylformamide; ketones, e.g. acetone or methyl ethyl ketone, and if appropriate also water and mixture of these. It is also possible for the compounds of the formulae III, IV and V to be used in excess as the solvent. Advantageously, the solvent is used in an amount of from 100 to 2000, preferably from 200 to 700%, by weight, based on starting material II.

All conventional acid acceptors can be used as inorganic or organic bases for the reaction to give compounds of the formula I. These preferably include tertiary amines, alkaline earth metal compounds, ammonium compounds and alkali metal compounds, as well as mixtures of these. However, it is also possible to use zinc compounds. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, tripropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, alphapicoline, $\beta$-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurylamine and triethylenediamine.

The acid acceptor is advantageously used in an amount of from 80 to 120%, based on the starting material IV or VI.

Preferred reaction accelerators are metal halides, such as sodium iodide or potassium iodide.

An example of leaving group X which can be displaced by nucleophilic substitution is halogen.

All organic and inorganic acids which form phytophysiologically tolerated salts are suitable for salt formation with compounds of the formula I. Examples are chlorides, bromides, iodides, sulfates, phosphates, acetates, oxalates, fumarates, malonates, alkylsulfonates, arylsulfonates and dodecylbenzenesulfonates.

The salts are obtained by combining the appropriate acid with a free amine of the formula I in the presence or absence of an inert solvent, separating off the solvent and, if required, recrystallizing the residue.

The starting materials of the formulae III, V and VIII are well known and/or can be prepared by conventional methods. Aldehydes of the formula II and halides of the formula VI (where X is chlorine or bromine) are disclosed in European Pat. No. 9,977.

The Examples which follow illustrate the preparation of the compounds of the formula I.

EXAMPLE 1

(a) 204 g of 3-(4'-tert-butylphenyl)-2-methylpropionaldehyde are added dropwise to a solution of 71 g of n-butylamine in 800 ml of ethanol at 25° C. Stirring is carried out for 36 hours at 25° C., after which 87 g of sodium borohydride are added a little at a time to the mixture, and stirring is continued for a further 4 hours at 78° C. The mixture is cooled, diluted with 1.5 l of water and extracted with three times 300 ml of methylene chloride. The combined extracts are washed with 300 ml of water, dried and distilled to give 170 g of N-butyl-N-3-(1-(4'-tert-butylphenyl)-2-methyl)-propylamine of boiling point 125° C./0.4 mbar (compound No. 1).

(b) 2 g of potassium iodide are added to a solution of 22.4 g of 3-(4'-tert-butylphenyl)-2-methylpropyl chloride in 36.5 g of n-butylamine, and the mixture is stirred under reflux for 48 hours. The reaction mixture is cooled to +10° C., after which 100 ml of 20 percent strength by weight aqueous sodium hydroxide solution are added, the mixture is stirred for 10 minutes at 25° C. and the organic phase is separated off and subjected to fractional distillation under reduced pressure. 25 g of N-butyl-N-3-(1-(4'-tert-butylphenyl)-2-methyl)-propylamine of boiling point 110° C./0.15 mbar are obtained (compound No. 1).

The compounds listed below can be obtained in a similar manner by selecting the starting materials and appropriately adapting the process conditions:

TABLE 1

| Compound no. | $R^1$ | $R^2$ | $R^3$ | $R^4$ | $R^5$ | Refractive index or b.p. [°C./mbar] |
|---|---|---|---|---|---|---|
| 2 | tert.-$C_4H_9$ | H | H | —$CH_3$ | —$CH_3$ | 145/10 |
| 3 | tert.-$C_4H_9$ | H | H | —$CH_3$ | —$C_2H_5$ | 118–119/3.0 |
| 4 | tert.-$C_4H_9$ | H | H | —$CH_3$ | i-$C_3H_7$ | 130–140/5.0 |
| 5 | F | H | H | —$CH_3$ | n-$C_3H_7$ | 80–82/0.1 |
| 6 | —$CH_3$ | H | H | —$CH_3$ | n-$C_3H_7$ | 90–92/0.1 |
| 7 | tert.-$C_4H_9$ | H | H | —$CH_3$ | n-$C_3H_7$ | 120–12/0.2 |
| 8 | Cl | 2-Cl | H | n-$C_4H_9$ | n-$C_3H_7$ | 144/0.1 |
| 9 | $CH_3$—O— | H | H | —$CH_3$ | n-$C_3H_7$ | 128–135/2 |
| 10 | $CH_3$—O— | H | H | —$CH_3$ | n-$C_4H_9$ | 130–134/0.4 |
| 11 | H | H | H | n-$C_3H_7$ | n-$C_4H_9$ | 110–112/0.3 |
| 12 | H | H | H | n-$C_4H_9$ | n-$C_4H_9$ | 124/0.5 |
| 13 | Cl | H | H | —$CH_3$ | n-$C_4H_9$ | 109–112/0.4 |
| 14 | H | 2-F | H | —$CH_3$ | n-$C_4H_9$ | 100–105/0.4 |
| 15 | Cl | 2-Cl | H | —$CH_3$ | n-$C_4H_9$ | 136–140/0.4 |
| 16 | Cl | 2-Cl | H | —$CH_3$ | iso-$C_4H_9$ | 136–138/0.2 |
| 17 | Cl | 2-Cl | —$CH_3$ | —$CH_3$ | n-$C_4H_9$ | 122–125/0.1 |
| 18 | Cl | H | —$C_2H_5$ | $C_2H_5$ | n-$C_4H_9$ | 137–140/0.3 |
| 19 | tert.-$C_4H_9$ | H | H | —$CH_3$ | tert.-$C_4H_9$ | 91–100/5 |
| 20 | $C_2H_5(CH_3)_2C$— | H | H | —$CH_3$ | n-$C_4H_9$ | 148–154/2 |
| 21 | n-$C_3H_7(CH_3)_2C$— | H | H | —$CH_3$ | n-$C_4H_9$ | 140–148/0.4 |
| 22 | 2-norbornyl | H | H | —$CH_3$ | n-$C_4H_9$ | 164–172/0.3 |
| 23 | tert.-$C_4H_9$ | H | H | —$CH_3$ | n-$C_5H_{11}$ | $n_D^{22}$: 1.4886 |
| 24 | tert.-$C_4H_9$ | H | H | —$CH_3$ | —$CH_2CH_2CH(CH_3)_2$ | $n_D^{22}$: 1.4904 |
| 25 | tert.-$C_4H_9$ | H | H | —$CH_3$ | —$CH(CH_3)C_4H_9$-n | $n_D^{22}$: 1.4878 |
| 26 | tert.-$C_4H_9$ | H | H | —$CH_3$ | n-$C_6H_{13}$ | $n_D^{22}$: 1.4808 |
| 27 | tert.-$C_4H_9$ | H | H | —$CH_3$ | —$CH_2CH(C_2H_5)_2$ | $n_D^{22}$: 1.49903 |
| 28 | tert.-$C_4H_9$ | H | H | —$CH_3$ | —$C(CH_3)_2CH(CH_3)_2$ | $n_D^{23}$: 1.4928 |
| 29 | tert.-$C_4H_9$ | H | H | —$CH_3$ | —$CH(CH_3)CH(CH_3)C_2H_5$ | $n_D^{25}$: 1.4909 |
| 30 | tert.-$C_4H_9$ | H | H | —$CH_3$ | —$CH_2CH(CH_3)C_3H_7$-n | $n_D^{22}$: 1.4882 |
| 31 | H | H | H | n-$C_3H_7$ | n-$C_6H_{13}$ | 130–134/0.5 |
| 32 | H | H | H | n-$C_4H_9$ | n-$C_6H_{13}$ | 145–152/0.4 |
| 33 | H | 2-F | H | —$CH_3$ | —$C_6H_{13}$ | 125–128/0.4 |
| 34 | Cl | H | H | —$CH_3$ | n-$C_6H_{13}$ | 140–143/0.4 |
| 35 | Cl | 2-Cl | H | —$CH_3$ | n-$C_6H_{13}$ | 152–154/0.3 |
| 36 | $C_2H_5(CH_3)_2C$— | H | H | —$CH_3$ | n-$C_6H_{13}$ | 165–167/0.5 |
| 37 | n-$C_3H_7(CH_3)_2C$— | H | H | —$CH_3$ | n-$C_6H_{13}$ | 160–162/0.4 |
| 38 | n-$C_4H_9(CH_3)_2C$— | H | H | —$CH_3$ | n-$C_6H_{13}$ | 172–180/0.5 |
| 39 | $(CH_3)_2CHC(CH_3)_2$— | H | H | —$CH_3$ | n-$C_6H_{13}$ | 159–161/0,4 |
| 40 | 2-norbornyl | H | H | —$CH_3$ | n-$C_6H_{13}$ | 194–196/0,4 |
| 41 | tert.-$C_4H_9$ | H | H | —$CH_3$ | —$CH(CH_3)C_5H_{11}$-n | $n_D^{22}$: 1,48865 |
| 42 | tert.-$C_4H_9$ | H | H | —$CH_3$ | —$CH(CH_3)CH_2CH_2CH(CH_3)_2$ | $n_D^{22}$: 1,4860 |
| 43 | tert.-$C_4H_9$ | H | H | —$CH_3$ | —$CH(C_2H_5)C_4H_9$-n | $n_D^{25}$: 1,4876 |
| 44 | tert.-$C_4H_9$ | H | H | —$CH_3$ | n-$C_8H_{17}$ | 166–168/0,3 |
| 45 | tert.-$C_4H_9$ | H | H | —$CH_3$ | —$CH_2$—$CH(CH_3)C_4H_9$-n | $n_D^{22}$: 1,4872 |
| 46 | tert.-$C_4H_9$ | H | H | —$CH_3$ | —$C(CH_3)_2CH_2C(CH_3)_3$ | $n_D^{23}$: 1,4952 |
| 47 | tert.-$C_4H_9$ | H | H | —$CH_3$ | $\begin{array}{c}H\\|\\-CCH_2CH_2-CH(CH_3)CH_2C(CH_3)_3\\|\\H\end{array}$ | $n_D^{22}$: 1,4871 |
| 48 | Cl | 2-Cl | H | —$CH_3$ | n-$C_{12}H_{25}$ | 190–194/0,1 |
| 49 | tert.-$C_4H_9$ | H | H | —$CH_3$ | —$CH_2CH=CH_2$ | |
| 50 | tert.-$C_4H_9$ | H | H | —$CH_3$ | —$CH(CH_3)CH(CH_3)_2$ | |
| 51 | tert.-$C_4H_9$ | H | H | —$CH_3$ | —$CH_2$—$CH_2$—$CH=CH_2$ | |
| 52 | tert.-$C_4H_9$ | H | H | —$CH_3$ | —$CH_2$—$CH=C(CH_3)_2$ | |
| 53 | tert.-$C_4H_9$ | H | H | —$CH_3$ | —$CH_2$—$CH_2$—$C(CH_3)=CH_2$ | |
| 54 | tert.-$C_4H_9$ | H | H | —$CH_3$ | -cyclopentyl | 138–145/3 |
| 55 | tert.-$C_4H_9$ | H | H | —$CH_3$ | —$CH(CH_3)$cyclopropyl | |
| 56 | tert.-$C_4H_9$ | H | H | —$CH_3$ | 2,4,4-trimethylcyclopentyl | 145–153/3 |
| 57 | tert.-$C_4H_9$ | H | H | —$CH_3$ | -cyclohexyl | 148–160/5 |
| 58 | Cl | 2-Cl | H | —$CH_3$ | -cyclohexyl | 154–156/0.4 |
| 59 | tert.-$C_4H_9$ | H | H | —$CH_3$ | 3-methylcyclohexyl | 144–152/5 |
| 60 | tert.-$C_4H_9$ | H | H | —$CH_3$ | 4-methylcyclohexyl | 170–190/5 |

TABLE 1-continued

| Compound no. | R¹ | R² | R³ | R⁴ | R⁵ | Refractive index or b.p. [°C./mbar] |
|---|---|---|---|---|---|---|
| 61 | tert.-C₄H₉ | H | H | —CH₃ | 2,4-dimethylcyclohexyl | 150–160/1 |
| 62 | tert.-C₄H₉ | H | H | —CH₃ | 2,5-dimethylcyclohexyl | 150–160/5 |
| 63 | tert.-C₄H₉ | H | H | —CH₃ | 2,6-dimethylcyclohexyl | 153–160/1 |
| 64 | tert.-C₄H₉ | H | H | —CH₃ | 3,5-dimethylcyclohexyl | 162–172/5 |
| 65 | tert.-C₄H₉ | H | H | —CH₃ | 3,3,5-trimethylcyclohexyl | 143–155/0.3 |
| 67 | tert.-C₄H₉ | H | H | —CH₃ | 2-methyl-6-ethylcyclohexyl | 143–150/0.5 |
| 68 | tert.-C₄H₉ | H | H | —CH₃ | 2,6-diethylcyclohexyl | 186–192/4 |
| 69 | tert.-C₄H₉ | H | H | —CH₃ | 4-isopropylcyclohexyl | 200–210/5 |
| 70 | tert.-C₄H₉ | H | H | —CH₃ | —CH₂-cyclohexyl | $n_D^{25}$: 1.5086 |
| 71 | tert.-C₄H₉ | H | H | —CH₃ | —CH(CH₃)CH₂-cyclohexyl | 165–170/3 |
| 72 | tert.-C₄H₉ | H | H | —CH₃ | —CH₂CH(C₂H₅)CH₂CH(CH₃)-cyclohexyl | 205–215/3 |
| 73 | tert.-C₄H₉ | H | H | —CH₃ | cyclooctyl | $n_D^{22}$: 1.5154 |
| 74 | tert.-C₄H₉ | H | H | —CH₃ | 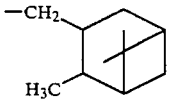 | 260–275/5 |
| 75 | tert.-C₄H₉ | H | H | —CH₃ | 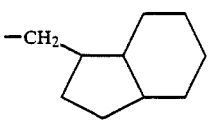 | 250–277/5 |
| 76 | tert.-C₄H₉ | H | H | —CH₃ |  | $n_D^{22}$: 1.5127 |
| 77 | tert.-C₄H₉ | H | H | —CH₃ | 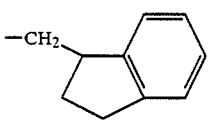 | 247–260/5 |
| 78 | tert.-C₄H₉ | H | H | —CH₃ | —C₆H₅ | 188–195/4 |
| 79 | tert.-C₄H₉ | H | H | —CH₃ | 4-Cl—C₆H₄— | 168–180/0.1 |
| 80 | tert.-C₄H₉ | H | H | —CH₃ | 3,4-Cl₂C₆H₃— | 225–230/4 |
| 81 | tert.-C₄H₉ | H | H | —CH₃ | 3,5-Cl₂C₆H₃— | 183–195/0.1 |
| 82 | tert.-C₄H₉ | H | H | —CH₃ | 3-(CH₃)C₆H₄— | 170–150/3 |
| 83 | tert.-C₄H₉ | H | H | —CH₃ | 4-(CH₃)C₆H₄— | 162–170/0.1 |
| 84 | tert.-C₄H₉ | H | H | —CH₃ | 2,4-(CH₃)₂C₆H₃— | 165–175/3 |
| 85 | tert.-C₄H₉ | H | H | —CH₃ | 2,5-(CH₃)₂C₆H₃— | 200–210/4 |
| 86 | tert.-C₄H₉ | H | H | —CH₃ | 2,6-(CH₃)₂C₆H₃— | 192–210/3 |
| 87 | tert.-C₄H₉ | H | H | —CH₃ | 3,5-(CH₃)₂C₆H₃— | 171–181/0.1 |
| 88 | tert.-C₄H₉ | H | H | —CH₃ | 4-C9-C₃H₇)C₆H₄— | 205–215/4 |
| 89 | tert.-C₄H₉ | H | H | —CH₃ | 2-(CH₃), 6-(C₂H₅)C₆H₃— | 215–218/1 |
| 90 | tert.-C₄H₉ | H | H | —CH₃ | 2,6-(C₂H₅)₂C₆H₃— | 190–195/3 |
| 91 | tert.-C₄H₉ | H | H | —CH₃ | 3-(CF₃)C₆H₄— | 160–170/0.3 |
| 92 | tert.-C₄H₉ | H | H | —CH₃ | 3,5-(CF₃)₂C₆H₃— | 170–180/3 |
| 93 | tert.-C₄H₉ | H | H | —CH₃ | 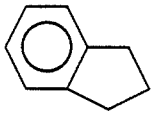 | 200–215/5 |
| 94 | tert.-C₄H₉ | H | H | —CH₃ | —CH₂—C₆H₅ | 215–220/5 |
| 95 | tert.-C₄H₉ | H | H | —CH₃ | —CH(CH₃)C₆H₅ | 160–170/3 |
| 96 | tert.-C₄H₉ | H | H | —CH₃ | —CH(C₃H₇)nC₆H₅ | 160–170/3 |
| 97 | tert.-C₄H₉ | H | H | —CH₃ | 4-ClC₆H₄—CH₂— | |
| 98 | tert.-C₄H₉ | H | H | —CH₃ | 4-(CH₃C₆H₄—CH₂— | |
| 99 | tert.-C₄H₉ | H | H | —CH₃ | 2,4-Cl₂C₆H₃—CH₂— | |
| 100 | tert.-C₄H₉ | H | H | —CH₃ | 3,4-Cl₂C₆H₃—CH₂— | |
| 101 | tert.-C₄H₉ | H | H | —CH₃ | 2,4-(CH₃)₂C₆H₃— | |
| 102 | tert.-C₄H₉ | H | H | —CH₃ | C₆H₅—CH₂CH₂— | |
| 103 | tert.-C₄H₉ | H | H | —CH₃ | C₆H₅—CH(CH₃)CH₂— | |
| 104 | tert.-C₄H₉ | H | H | —CH₃ | 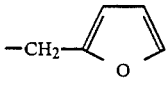 | 180–200/3 |
| 105 | tert.-C₄H₉ | H | H | —CH₃ | —CH(CH₃)CH₂—C₆H₅ | 210–215/3 |

TABLE 1-continued

| Compound no. | $R^1$ | $R^2$ | $R^3$ | $R^4$ | $R^5$ | Refractive index or b.p. [°C./mbar] |
|---|---|---|---|---|---|---|
| 106 | tert.-$C_4H_9$ | H | H | —$CH_3$ | —$CH(CH_3)CH(CH_3)C_6H_5$ | 172–180/3 |
| 107 | tert.-$C_4H_9$ | H | H | —$CH_3$ | —$CH(CH_3)CH_2CH_2C_6H_5$ | 210–220/1 |
| 108 | tert.-$C_4H_9$ | H | H | —$CH_3$ | —$CH_2CH_2CH(CH_3)CH_2CH_2CH_2C(CH_3)_2$ | $n_D^{22}$: 1.4966 |
| 109 | tert.-$C_4H_9$ | H | H | —$CH_3$ | —$CH(CH_3)CH_2CH(CH_3)C_2H_5$ | $n_D^{22}$: 1.4822 |
| 110 | tert.-$C_4H_9$ | H | H | —$CH_3$ | —$CH_2$—$C(CH_3)_3$ | nhd $D^{22}$: 1.4972 |
| 111 | tert.-$C_4H_9$ | H | H | —$CH_3$ | —$CH(C_2H_5)_2$ | 110–125/0.2 |
| 112 | tert.-$C_4H_9$ | H | H | —$CH_3$ | —$CH(CH_3)CH_2CH(CH_3)_2$ | 145–148/0.4 |

TABLE 2

$$\text{structure with cyclohexyl-}R^1\text{, }R^3R^4\text{, }NH-R^5$$

| Compound no. | $R^1$ | $R^3$ | $R^4$ | $R^5$ | Refractive index or b.p. [°C./mbar] |
|---|---|---|---|---|---|
| 113 | tert.-$C_4H_9$ | H | —$CH_3$ | —$CH_3$ | |
| 114 | tert.-$C_4H_9$ | H | —$CH_3$ | —$C_2H_5$ | |
| 115 | tert.-$C_4H_9$ | H | —$CH_3$ | i-$C_3H_7$ | |
| 116 | tert.-$C_4H_9$ | H | —$CH_3$ | n-$C_3H_7$ | |
| 117 | tert.-$C_4H_9$ | H | —$CH_3$ | n-$C_5H_{11}$ | |
| 118 | tert.-$C_4H_9$ | H | —$CH_3$ | —$CH_2CH_2CH(CH_3)_2$ | |
| 119 | tert.-$C_4H_9$ | H | —$CH_3$ | —$CH(CH_3)C_4H_9$-n | |
| 120 | tert.-$C_4H_9$ | H | —$CH_3$ | n-$C_6H_{13}$ | |
| 121 | tert.-$C_4H_9$ | H | —$CH_3$ | —$CH_2CH(C_2H_5)_2$ | |
| 122 | tert.-$C_4H_9$ | H | —$CH_3$ | —$C(CH_3)_2CH(CH_3)_2$ | |
| 123 | tert.-$C_4H_9$ | H | —$CH_3$ | —$CH(CH_3)CH(CH_3)C_2H_5$ | |
| 124 | tert.-$C_4H_9$ | H | —$CH_3$ | —$CH_2CH(CH_3)C_3H_7$-n | |
| 125 | tert.-$C_4H_9$ | H | —$CH_3$ | —$CH(CH_3)C_5H_{11}$-n | |
| 126 | tert.-$C_4H_9$ | H | —$CH_3$ | —$CH(CH_3)CH_2CH_2CH(CH_3)_2$ | |
| 127 | tert.-$C_4H_9$ | H | —$CH_3$ | —$CH(C_2H_5)C_4H_9$-n | |
| 128 | tert.-$C_4H_9$ | H | —$CH_3$ | n-$C_8H_{17}$ | |
| 129 | tert.-$C_4H_9$ | H | —$CH_3$ | —$CH_2$—$CH(CH_3)C_4H_9$-n | |
| 130 | tert.-$C_4H_9$ | H | —$CH_3$ | —$C(CH_3)_2CH_2C(CH_3)_3$ | |
| 131 | tert.-$C_4H_9$ | H | —$CH_3$ | H–C(—$CH_2CH_2$—$CH(CH_3)CH_2C(CH_3)_3$)–H | |
| 132 | tert.-$C_4H_9$ | H | —$CH_3$ | —$CH_2$—$CH$=$CH_2$ | |
| 133 | tert.-$C_4H_9$ | H | —$CH_3$ | —$CH_2$—$CH$=$CH$—$CH_3$ | |
| 134 | tert.-$C_4H_9$ | H | —$CH_3$ | —$CH_2$—$CH_2$—$CH$=$CH_2$ | |
| 135 | tert.-$C_4H_9$ | H | —$CH_3$ | —$CH_2$—$CH$=$C(CH_3)_2$ | |
| 136 | tert.-$C_4H_9$ | H | —$CH_3$ | —$CH_2$—$CH_2$—$C(CH_3)$=$CH_2$ | |
| 137 | tert.-$C_4H_9$ | H | —$CH_3$ | -cyclopentyl | |
| 138 | tert.-$C_4H_9$ | H | —$CH_3$ | —$CH(CH_3)$cyclopropyl | |
| 139 | tert.-$C_4H_9$ | H | —$CH_3$ | 2,4,4-trimethylcyclopentyl | |
| 140 | tert.-$C_4H_9$ | H | —$CH_3$ | -cyclohexyl | 160–163/0.3 |
| 141 | tert.-$C_4H_9$ | H | —$CH_3$ | 3-methylcyclohexyl | |
| 142 | tert.-$C_4H_9$ | H | —$CH_3$ | 4-methylcyclohexyl | |
| 143 | tert.-$C_4H_9$ | H | —$CH_3$ | 2,4-dimethylcyclohexyl | |
| 144 | tert.-$C_4H_9$ | H | —$CH_3$ | 2,5-dimethylcyclohexyl | |
| 145 | tert.-$C_4H_9$ | H | —$CH_3$ | 2,6-dimethylcyclohexyl | |
| 146 | tert.-$C_4H_9$ | H | —$CH_3$ | 3,5-dimethylcyclohexyl | |
| 147 | tert.-$C_4H_9$ | H | —$CH_3$ | 3,3,5-trimethylcyclohexyl | 145–147/1 |
| 148 | tert.-$C_4H_9$ | H | —$CH_3$ | 2,3,6-trimethylcyclohexyl | |
| 149 | tert.-$C_4H_9$ | H | —$CH_3$ | 2-methyl-6-ethylcyclohexyl | |
| 150 | tert.-$C_4H_9$ | H | —$CH_3$ | 2,6-diethylcyclohexyl | |
| 151 | tert.-$C_4H_9$ | H | —$CH_3$ | 4-isopropylcyclohexyl | |
| 152 | tert.-$C_4H_9$ | H | —$CH_3$ | —$CH_2$-cyclohexyl | |
| 153 | tert.-$C_4H_9$ | H | —$CH_3$ | —$CH(CH_3)CH_2$-cyclohexyl | |
| 154 | tert.-$C_4H_9$ | H | —$CH_3$ | —$CH_2CH(C_2H_5)CH_2CH(CH_3)$-cyclohexyl | |
| 155 | tert.-$C_4H_9$ | H | —$CH_3$ | -cyclooctyl | |

In general terms, the novel compounds are very effective against a broad spectrum of phytopathogenic fungi, in particular those from the class consisting of the Ascomycetes and Basidiomycetes. Some of them have a systemic action and can be used as foliar and soil fungicides.

the fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and for vegetables, such as cucumbers, beans and Cucurbitaceae.

The novel compounds are particularly useful for controlling the following plant diseases:
*Erysiphe graminis* in cereals,

*Erysiphe cichoracearum* and *Sphaerotheca fuliginea* in Cucurbitaceae,
*Podosphaera leucotricha* in apples,
*Uncinula necator* in vines,
Puccinia species in cereals,
*Rhizoctonia solani* in cotton and lawns,
Ustilago species in cereals and sugar cane,
*Venturia inaequalis* (scab) in apples,
*Septoria nodorum* in wheat,
*Pyrenophora teres* in barley,
*Botrytis cinerea* (gray mold) in strawberries and vines,
*Cercospora musae* in bananas,
*Pseudocercosporella herpotrichoides* in wheat and barley,
*Pyricularia oryzae* in rice,
*Hemileia vastatrix* in coffee,
*Alternaria solani* in potatoes and tomatoes,
*Plasmopara viticola* in vines, and
Fusarium and Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The forms for use depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (e.g. xylene or benzene), chlorinated aromatics (e.g. chlorobenzenes), paraffins (e.g. oil fractions), alcohols (e.g. methanol or butanol), ketones (e.g. cyclohexanone), amines (e.g. ethanolamine or dimethylformamide) and water; carriers, such as ground natural minerals (kaolins, aluminas, talc or chalk) and ground synthetic minerals (e.g. highly disperse silica or silicates); emulsifiers, such as nonionic and anionic emulsifiers (e.g. polyoxyethylene fatty alcohol ethers, alkylsulfonates and arylsulfonates) and dispersants, such as lignin, sulfite waste liquors and methylcellulose.

The fungicides generally contain for 0.1 to 95, preferably from 0.5 to 90, % by weight of active ingredient.

The agents and the ready-to-use formulations prepared from them, such as solutions, emulsions, suspensions, powders, dusts, pastes or granules, are applied in a conventional manner, for example by spraying, atomizing, dusting, scattering, dressing or watering.

Examples of such formulations are:

I. 90 parts by weight of compound no. 3 is mixed with 10 parts by weight of N-methyl-alpha-pyrrolidone. A mixture is obtained which is suitable for application in the form of very fine drops.

II. 20 parts by weight of compound no. 23 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 24 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 32 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 34 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 36 is intimately mixed with 97 parts by weight of particulate kaolin. A dust is obtained containing 3% by weight of the active ingredient.

VII. 30 parts by weight of compound no. 37 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 39 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 40 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides, ammonia complex of zinc N,N'-ethylenebisdithiocarbamate,
ammonia complex of zinc N,N'-propylenebisdithiocarbamate,
zinc N,N'-propylenebisdithiocarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[bis-(dimethylamino)-phosphinyl]-3-phenyl-1,2,4triazole,
2,3-dicyano-1,4-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)butan-2-one,
1-(1-chlorophenoxy)-3,3-dimethyl-1-(1H-1,2,4-triazol-1-yl)butan-2-ol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-β-(1H-1,2,4-triazol-1-ylmethyl)-benzhydryl alcohol.

For the following experiments, the prior art active ingredient N-tridecyl-2,6-dimethylmorpholine (A) was used for comparison purposes.

USE EXAMPLE 1

Action on powdery mildew of wheat

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of powdery mildew of wheat (Erysiphe graminis var. tritici). The test plants were then placed in a greenhouse at from 20° to 22° C. and from 75 to 80% relative humidity. After 7 days, the extent of powdery mildew spread was determined.

The results show that, when used as a liquor containing the active ingredient in concentrations of 0.025 and 0.006 wt. %, compound nos. 3, 20, 23, 24, 32, 34, 36, 37, 39, 40, 41, 42 and 44 had a better fungicidal action (97%) than prior art active ingredient A (90%).

USE EXAMPLE 2

Action on cucumber powdery mildew

Young cucumber plants of the Chinesische Schlange variety, in the two-leaf stage, were sprayed with an aqueous conidial suspension of cucumber powdery mildew. After 20 hours, these plants were sprayed to run-off with an aqueous spray liquor containing (dry basis) 80% of active ingredient and 20% of emulsifier, and were placed in a greenhouse at from 20° to 22° C. and 70–80% humidity. 21 days after application of the active ingredient, the extent of fungal infestation was determined.

The results show that, when used as a liquor containing the active ingredient in a concentration of 0.025%, compound nos. 20, 21, 23, 25, 26, 27, 36, 44, 70 and 140 had a better fungicidal action (97%) than prior art active ingredient A (60%).

USE EXAMPLE 3

Action on wheat brown rust

Leaves of pot-grown wheat seedlings of the Frühgold variety were dusted with spores of brown rust (*Puccinia recondita*). The pots were then placed in a chamber at from 20° to 22° C. and with a high humidity (90-95%) for 24 hours. During this time, the spores germinated, and the germ tubes penetrated into the leaf tissue. The infected plants were then sprayed to runoff with aqueous spray liquors containing (dry basis) 80% of active ingredient and 20% of emulsifier. When the spray coating had dried on, the test plants were placed in a greenhouse at from 20° to 22° C. and from 65 to 70% relative humidity. After 8 days the extent of development of rust fungi on the leaves was determined.

The results show that, when used as a liquor containing the active ingredient in a concentration of 0.025%, compound nos. 7, 8, 15, 16, 17, 20, 23, 24, 25, 26, 27, 28, 36, 37, 39, 41, 42, 44, 45 and 73 had a better fungicidal action (97%) than the prior art active ingredient A (50%).

USE EXAMPLE 4

Action on Plasmopara viticola

Leaves of potted vines of the Mueller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that, when used for instance as a liquor containing the active ingredient in a concentration of 0.05%, compound nos. 11, 15, 22, 23, 24, 26, 28, 31, 32, 36, 41, 44, 71 and 140 had a better fungicidal action (97%) than prior art active ingredient A (50%).

We claim:

1. An N-arylpropyl-substituted secondary amine of the formula

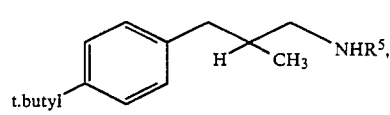

where $R^5$ is alkyl of 1 to 10 carbon atoms, cycloalkyl of 3 to 12 carbon atoms, cycloalkenyl of 5 to 12 carbon atoms, cycloalkylalkyl of 4 to 13 carbon atoms, alkenyl of 3 to 6 carbon atoms or a phenyl or phenyl-$C_1$-$C_6$-alkyl radical which is unsubstituted or substituted by halogen, $C_1$-$C_4$-alkyl, halo-$C_1$-$C_4$-alkyl, $C_1$-$C_4$-alkoxy or cyano, or a salt thereof.

2. A fungicide containing a solid or liquid carrier and a compound as set forth in claim 1.

* * * * *